Figure 1:
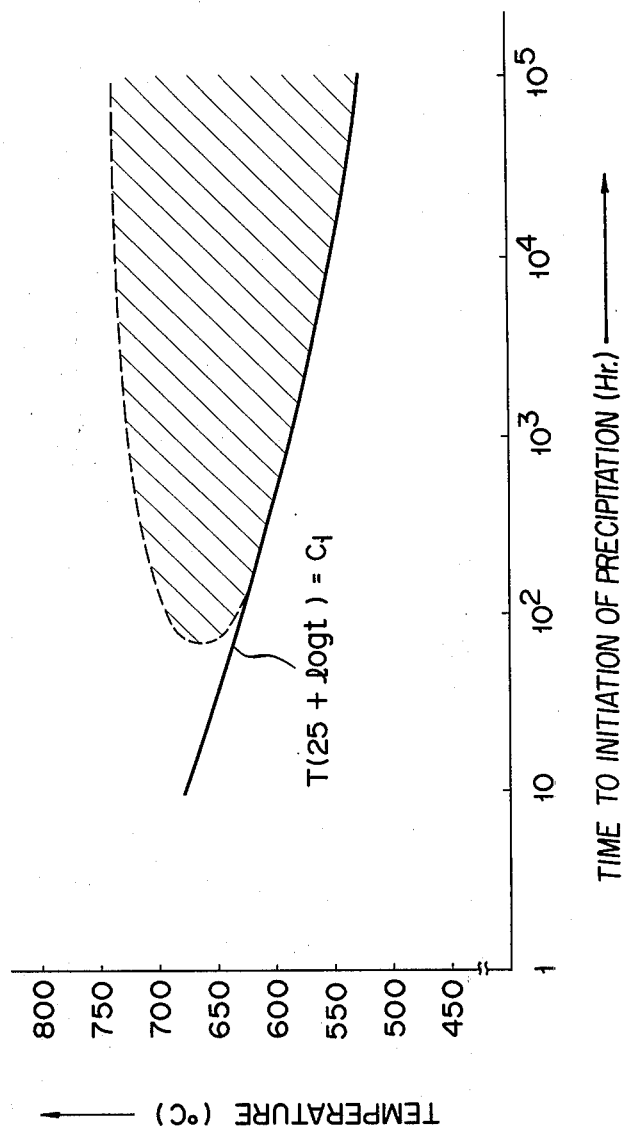

United States Patent [19]

Komatsu et al.

[11] 4,321,821

[45] Mar. 30, 1982

[54] METHOD OF ESTIMATING THE RESIDUAL LIFE OF HEAT RESISTANT PARTS MADE OF 12% Cr STEELS

[75] Inventors: Shuichi Komatsu, Yokohama; Masako Nakahashi, Kawasaki; Hiromitsu Takeda, Yokosuka; Masayuki Yamada, Yokohama, all of Japan

[73] Assignee: Tokyo Shibaura Denki Kabushiki Kaisha, Kawasaki, Japan

[21] Appl. No.: 109,313

[22] Filed: Jan. 3, 1980

[30] Foreign Application Priority Data

Jan. 31, 1979 [JP] Japan .................................. 54/9121

[51] Int. Cl.³ ............................................. G01N 25/00
[52] U.S. Cl. ................................................. 73/15 R
[58] Field of Search ..................... 73/15 R, 15.4, 15.6, 73/116; 148/128; 250/273

[56] References Cited

U.S. PATENT DOCUMENTS 3,950,985  4/1976  Buchwald .............................. 73/116
4,046,002  9/1977  Murphy et al. ....................... 73/116

OTHER PUBLICATIONS

Koutsky et al., "High—Temperature Properties of 12% Cr Steel alloyed with Tungsten, Molybdenum, and Vanadium" in the Journal of The Iron and Steel Institute 7/65 pp. 707-714.

*Primary Examiner*—Herbert Goldstein
*Attorney, Agent, or Firm*—Oblon, Fisher, Spivak, McClelland & Maier

[57] ABSTRACT

Disclosed is a method of measuring the deterioration degree of heat resistant parts made of a 12% Cr steel containing at least one of Mo and W and used under high temperatures on the basis of the amount of Laves phase precipitated within said 12% Cr steel.

4 Claims, 2 Drawing Figures

METHOD OF ESTIMATING THE RESIDUAL LIFE OF HEAT RESISTANT PARTS MADE OF 12% Cr STEEL

This invention relates to a method of estimating or measuring the residual life of heat resistant parts made of 12% Cr steels used under high temperatures.

A blade of a steam turbine, which is generally made of a 12% Cr steels, is exposed to such high temperatures as, for example, 530° C. to 560° C. for a long period of time. The blade is gradually deteriorated with time, resulting in that the mechanical strength of the blade is lowered so much that accidents tend to be caused unless the blade is replaced. In order to prevent accidents, it is customary to examine periodically the degree of defects and deformation of turbine parts like a blade. However, a method of accurately detecting the deterioration degree of turbine parts or the like has not yet been developed. It is a matter of serious concern in this field to develop a method of accurately measuring the deterioration degree with time of heat resistant parts like a blade of a steam turbine, with the smallest breaking damage done to the heat resistant parts.

An object of this invention is to provide a method of easily and accurately measuring the deterioration degree with time of a 12% Cr steels containing at least one of Mo and W and used under high temperatures.

According to this invention, there is provided a method of measuring the deterioration degree of heat resistant parts made of a 12% Cr steels containing at least one of Mo and W and used under high temperatures on the basis of the amount of Laves phase precipitated within the alloy.

According to this invention, there is further provided a method of measuring the deterioration degree of heat resistant parts made of a 12% Cr steels, comprising the steps of:

(1) measuring the amount of Laves phase precipitated within the 12% Cr steel containing at least one of Mo and W and actually used under high temperatures, (2) obtaining the heating time of the same steel under an accelerated temperature, said heating time giving rise to precipitation of Laves phase in the same amount as measured in step (1), from a deterioration criterion curve denoting the relationship between the heating time of the steel under the accelerated temperature and the precipitated amount of Laves phase, and (3) converting the heating time under the accelerated temperature to the heating time under the actual operation temperature of the parts by using the following formula representing the recipitation behavior of Laves phase:

$$T(c+\log t)=C$$

where,
T is an absolute temperature,
t is a heating time,
c is a constant inherent in the steel material, and
C is constant determined by the precipitated amount of Laves phase.

The residual life of the heat resistant parts can be estimated by subtracting the value obtained through the above steps from the known value of the rupture time of the steel under the actual operation temperature of the parts.

Figure 2:
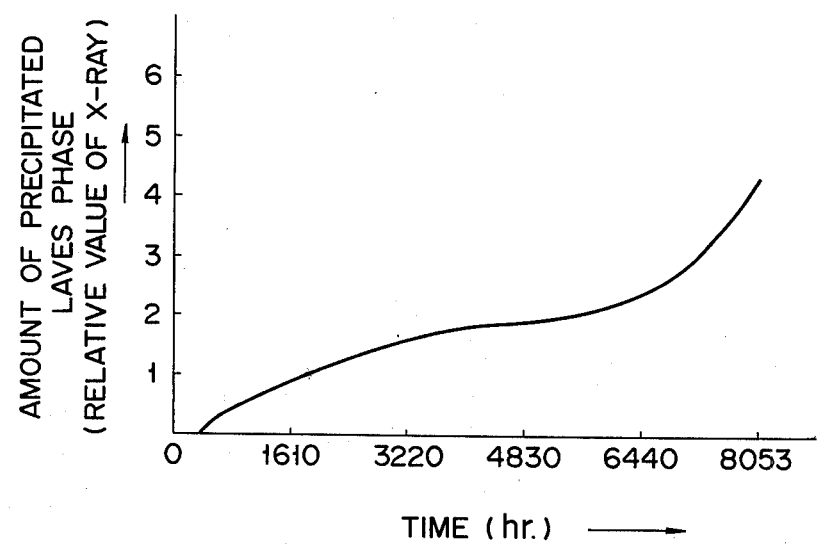

This invention can be more fully understood from the following detailed description when taken in conjunction with the accompanying drawings, in which:

FIG. 1 is a graph showing the precipitation behavior of Laves phase within a 12% Cr steel containing at least one of Mo and W relative to the temperature and heating time; and FIG. 2 is a graph (deterioration criterion curve) showing the relationship between the period of time during which the 12% Cr steel is subjected to an accelerated temperature and the amount of Laves phase precipitated within the steel.

12% Cr steels used as a blade of a steam turbine contain in general Mo and/or W in an amount of less than about 1% by weight. Naturally, parts such as a blade of a steam turbine are exposed to high temperatures during operation of the turbine. What should be noted is that, if a steam turbine part is formed of a steel of the above-mentioned type, carbides of $M_{23}C_6$(M representing an elemental metal contained in the steel) grow coarse with time and Laves phase, i.e., an intermetallic compound of $Fe_2Mo$ type, is precipitated in the form of a lump in mainly grain boundary. As a result of extensive researches on the precipitation behavior of Laves phase, it has been clarified that the precipitation behavior of Laves phase is substantially irrelevant to the stress exerted to the part but depends on the heating temperature and time of the part. FIG. 1 shows the relationship between the heating temperature and time with respect to the initiation of Laves phase precipitation within a 12% Cr steel containing at least one of Mo and W. The graph of FIG. 1 represents the following formula for the precipitation behavior of Laves phase:

$$T(c+\log t)=C_1$$

where,
c is a constant inherent in the steel material,
$C_1$ is a constant determined by the precipitation amount of Laves phase at the intital stage of precipitation,
T is an absolute temperature, and
t is a heating time.

A suitable value of the constant c is 25 when it comes to 12% Cr steels containing at least one of Mo and W. The shaded portion of FIG. 1 denotes a region within which Laves phase is precipitated. Within the Laves phase precipitation region, the relationship between the temperature and time giving rise to any amount of Laves phase precipitation is represented by the above formula, $T(c+\log t)=C$. To be brief, the precipitation amount of Laves phase, which is deeply related to the deterioration degree of the steel, depends on the heating temperature and time. In addition, the precipitation behavior of Laves phase can be represented by the above-mentioned formula involving the heating temperature and time as parameters. It follows that it is possible to estimate easily and accurately the deterioration degree and residual life of parts made of a 12% Cr steel.

According to a preferred embodiment of this invention, a deterioration criterion curve such as FIG. 2 is obtained in advance by measuring the relationship between the heating time under an accelerated temperature $T_2$ and the precipitated amount of Laves phase with respect to a 12% Cr steel containing at least one of Mo and W. On the other hand, measurement is taken of the amount of Laves phase precipitated within a part made of the 12% Cr steel actually used under a high temperature $T_1$. Then, time $t_2$ during which the same amount of Laves phase measured above is precipitated under the accelerated temperature $T_2$ is obtained from the deterioration criterion curve. Further, the time $t_2$ thus obtained is converted to time $t_1$ during which the part was actually used under the temperature $T_1$ by using the formula for the precipitation behavior of Laves phase as shown below:

$$T_1(25+\log t_1)=T_2(25+\log t_2)$$

Naturally, the residual life $L_R$ of the part made of the 12% Cr steel is obtained by subtracting the time $t_1$ from the creep rupture time $t_r$ of the 12% Cr steel under the temperature $T_1$: $L_R = t_r - t_1$. It is possible to use the known value of the creep rupture time. It is also possible to calculate the creep rupture time by using the deterioration criterion curve. Specifically, the rupture time at the accelerated temperature $T_2$ is obtained from the deterioration criterion curve and, then, converted to the rupture time at the temperature $T_1$ by using the formula for the precipitation behavior of Laves phase as exemplified above.

The precipitated amount of Laves phase can be determined by, for example, an X-ray diffraction method or a composition analysis method. In the X-ray diffraction method, a sample is electrolyzed for obtaining an X-ray diffraction pattern of the electrolysis residue containing carbides and Laves phase alone. For example, relative intensities of the (440) diffraction peak of $M_{23}C_6$ carbide and the (112) diffraction peak of Laves phase are obtained so as to determine the relative precipitation amount of Laves phase. In the composition analysis method, a sample is subjected to an electrolytic polishing, followed by observation with a scanning electron microscope for irradiating the precipitated material with an electron beam, thereby detecting the resultant characteristic X-rays. Since Laves phase is rich in Mo and W, it is possible to determine whether the precipitate consists of Laves phase or not. Thus, the absolute amount of the precipitated Laves phase can be determined by, for example, a picture image processing method of microphotograph.

The residual life of a heat resistant part was actually estimated by the invented method as described in the following example in order to show that the method of the present invention permits accurately estimating the residual life of the part.

Specifically, a creep test (15 Kb/mm² of stress) was applied to 12% Cr-Mo-W-V steel under an accelerated temperature of 590° C. The amount of Laves phase precipitated within the steel during the creep test was periodically measured by an X-ray diffraction method. The creep rupture time of the steel was found to be 8,053 hours. FIG. 2 shows a deterioration criterion curve obtained from the test results, i.e., a curve denoting the relationship between the heating time at the accelerated temperature of 590° C. and the precipitated amount of Laves phase.

On the other hand, a creep test (15 kg/mm² of stress) was also applied to another sample of the 12% Cr-Mo-W-V steel mentioned above under a temperature of 570° C. on the assumption that a steam turbine is exposed to said temperature during operation thereof. The sample was taken out 35,000 hours later and subjected to X-ray diffractometry, with the result that the precipitated amount of Laves phase was 3 in terms of the X-ray relative intensity. The deterioration criterion curve shown in FIG. 2 indicates that the value of 3 corresponds to about 7,000 hours of heating time under the accelerated temperature of 590° C. The heating time of 7,000 hours was converted to the heating time t under 570° C. by using the formula for the precipitation behavior of Laves phase as shown below:

$$(590+273)(\log 7{,}000+25)=(570+273)(\log t+25)$$
$$t \doteqdot 33{,}800 \text{ hours}$$

The rupture time of 12% Cr-Mo-W-V steel under 570° C. is already known to be about 38,000 hours. It follows that the residual life of the steel under 570° C. estimated by the invented method was:

38,000 hours − 33,800 hours ≐ 4,200 hours.

On the other hand, the rupture time of the steel under 570° C. obtained by a creep test was 39,452 hours. As mentioned previously, the sample was heated at 570° C. for 35,000 hours in the creep test described above. It follows that the actual residual life of the steel was:

39,452 hours − 35,000 hours = 4,452 hours.

The experiments described above substantiate that the method of the present invention permits accurately estimating the residual life of a 12% Cr steel.

What we claim is:

1. A method of measuring the deterioration degree of heat resistant parts made of a 12% Cr steel containing at least one of Mo and W and used under high temperatures, comprising the steps of:
    measuring the amount of Laves phase precipitated within the 12% Cr steel actually used under high temperatures;
    determining the heating time of the 12% Cr steel under an accelerated temperature, said heating time giving rise to precipitation of Laves phase in the same amount as measured in the preceding step, from a fixed predetermined standard which relates Laves phase precipitation to heating time; and
    converting the heating time under the accelerated temperature to the heating time under the actual operation temperature of the parts by using the following formula for the precipitation behavior of Laves phase:

$$T(c+\log t)=C$$

where,
    T is an absolute temperature,
    t is a heating time,
    c is a constant of 25 inherent in the steel material, and
    C is a constant determined by the precipitated amount of Laves phase.

2. A method of measuring the deterioration degree of heat resistant parts made of a 12% Cr steel containing at least one of Mo and W and used under high temperatures, comprising the steps of:
    measuring the amount of Laves phase precipitated within the 12% Cr steel actually used under high temperatures;
    obtaining the heating time of the 12% Cr steel under an accelerated temperature, said heating time giving rise to precipitation of Laves phase in the same amount as measured in the preceding step, from a deterioraton criterion curve representing the relationship between the heating time of the steel under the accelerated temperature and the amount of Laves phase precipitated during said heating time; and converting the heating time under the accelerated temperature to the heating time under the actual operation temperature of the parts by using the following formula for the precipitation behavior of Laves phase:

$$T(c + \log t) = C$$

where,

T is an absolute temperature, t is a heating time, c is a constant of 25 inherent in the steel material, and C is a constant determined by the precipitated amount of Laves phase.

3. The method according to claim 2, wherein the precipitated amount of Laves phase is measured by an X-ray diffractometry or composition analysis method.

4. The method according to claim 2, wherein the residual life of the parts is determined by subtracting the heating time under the actual operation temperature of the parts from the known value of rupture time of the 12% Cr steel under said temperature.

* * * * *